United States Patent
Lei et al.

(10) Patent No.: US 8,613,770 B2
(45) Date of Patent: Dec. 24, 2013

(54) ARTIFICIAL CERVICAL VERTEBRAE COMPOSITE JOINT

(75) Inventors: Wei Lei, Xi'an (CN); Baojun Han, Xi'an (CN); Zixiang Wu, Xi'an (CN); Da Liu, Xi'an (CN); Yabo Yan, Xi'an (CN); Jiangjun Zhou, Xi'an (CN); Xiong Zhao, Xi'an (CN); Suochao Fu, Xi'an (CN)

(73) Assignee: Wei Lei et al., Xi'an (CN)

( * ) Notice: Subject to any disclaimer, the term of this patent is extended or adjusted under 35 U.S.C. 154(b) by 0 days.

(21) Appl. No.: 13/388,748

(22) PCT Filed: Jul. 19, 2010

(86) PCT No.: PCT/CN2010/001083
§ 371 (c)(1),
(2), (4) Date: Apr. 13, 2012

(87) PCT Pub. No.: WO2011/015031
PCT Pub. Date: Feb. 10, 2011

(65) Prior Publication Data
US 2012/0197400 A1    Aug. 2, 2012

(30) Foreign Application Priority Data
Aug. 6, 2009   (CN) .......................... 2009 1 0023517

(51) Int. Cl.
*A61F 2/44*      (2006.01)

(52) U.S. Cl.
USPC ....................................................... 623/17.14

(58) Field of Classification Search
USPC ........................................... 623/17.11–17.16
See application file for complete search history.

(56) References Cited

U.S. PATENT DOCUMENTS

| | | | | |
|---|---|---|---|---|
| 5,246,458 A | * | 9/1993 | Graham | 623/17.14 |
| 5,480,442 A | * | 1/1996 | Bertagnoli | 623/17.14 |

(Continued)

FOREIGN PATENT DOCUMENTS

| | | |
|---|---|---|
| CN | 201040015 Y | 3/2008 |
| CN | 101627931 A | 1/2010 |
| CN | 201445571 U | 5/2010 |

OTHER PUBLICATIONS

"Optimal design and biomechanical assessment of 'artificial cervical joint complex'", J Fourth Mil Med Univ, 2009, 30(19), http://www.fmmuxb.cn, 1000-2790 (2009) Apr. 19, 2013, 1994-2009 China Academic Journal Electronic Publishing House, 4 pages.

(Continued)

*Primary Examiner* — Jan Christopher Merene
*Assistant Examiner* — Michelle C Eckman
(74) *Attorney, Agent, or Firm* — Westerman, Champlin & Koehler, P.A.

(57) ABSTRACT

An artificial cervical vertebrae composite joint is composed of two upper and lower fixing members disposed vertically symmetrically, a cervical vertebrae body member, and two connection members, the cervical vertebrae body member being connected between the fixing members through the connection members. The fixing members each have an L shape and comprise a front wing part and a base part. A locking screw hole is formed in the front wing part, and a skidproof groove provided with an inverted tooth and a protrusion is disposed on a middle portion of the base part. A bone grafting hole is transversely disposed through a middle portion of the cervical vertebrae body member, and two cavities are disposed on both upper and lower sides of the cervical vertebrae body member at an axial center of the cervical vertebrae body member to mount the connection members. The connection member has one end mounted in the cavity by means of a fixing ring, and another end connected with the fixing member to form a stable sliding-trough type ball-and-socket joint.

7 Claims, 5 Drawing Sheets

(56) References Cited

U.S. PATENT DOCUMENTS

| | | | |
|---|---|---|---|
| 5,534,029 A * | 7/1996 | Shima | 623/17.15 |
| 6,808,538 B2 * | 10/2004 | Paponneau | 623/17.16 |
| D581,055 S * | 11/2008 | Mateyka | D24/155 |
| 7,601,171 B2 * | 10/2009 | Ainsworth et al. | 623/17.11 |
| 7,744,650 B2 * | 6/2010 | Lindner et al. | 623/17.14 |
| 7,811,327 B2 * | 10/2010 | Hansell et al. | 623/17.15 |
| 7,938,858 B2 * | 5/2011 | Miller et al. | 623/17.14 |
| 7,959,678 B2 * | 6/2011 | Filippi et al. | 623/17.14 |
| 8,070,812 B2 * | 12/2011 | Keller | 623/17.11 |
| 8,070,816 B2 * | 12/2011 | Taylor | 623/17.15 |
| 8,088,164 B2 * | 1/2012 | Keller | 623/17.14 |
| 8,133,281 B2 * | 3/2012 | Lechmann et al. | 623/17.14 |
| 8,202,321 B2 * | 6/2012 | Gerner | 623/17.15 |
| 8,211,178 B2 * | 7/2012 | Melkent et al. | 623/17.16 |
| 8,268,004 B2 * | 9/2012 | Castleman et al. | 623/17.16 |
| 8,282,683 B2 * | 10/2012 | McLaughlin et al. | 623/17.11 |
| 2003/0045877 A1 * | 3/2003 | Yeh | 606/61 |
| 2003/0176925 A1 * | 9/2003 | Paponneau | 623/17.16 |
| 2003/0191534 A1 * | 10/2003 | Viart et al. | 623/17.15 |
| 2003/0220691 A1 * | 11/2003 | Songer et al. | 623/17.14 |
| 2003/0233146 A1 * | 12/2003 | Grinberg et al. | 623/17.14 |
| 2004/0117021 A1 | 6/2004 | Biedermann et al. | 623/17.15 |
| 2004/0186578 A1 * | 9/2004 | Mason | 623/17.16 |
| 2005/0004572 A1 * | 1/2005 | Biedermann et al. | 606/61 |
| 2005/0060034 A1 * | 3/2005 | Berry et al. | 623/17.11 |
| 2005/0060036 A1 * | 3/2005 | Schultz et al. | 623/17.15 |
| 2005/0228501 A1 * | 10/2005 | Miller et al. | 623/17.14 |
| 2006/0293755 A1 * | 12/2006 | Lindner et al. | 623/17.15 |
| 2008/0015704 A1 * | 1/2008 | Gradl et al. | 623/17.16 |
| 2009/0192618 A1 * | 7/2009 | Zielinski | 623/17.16 |
| 2010/0179655 A1 * | 7/2010 | Hansell et al. | 623/17.11 |
| 2011/0224794 A1 * | 9/2011 | Zielinski | 623/17.14 |
| 2012/0232659 A1 * | 9/2012 | Himmelberger et al. | 623/17.16 |
| 2012/0232660 A1 * | 9/2012 | Davenport | 623/17.16 |

OTHER PUBLICATIONS

International Search Report and Written Opinion (English translation for Search Report) for PCT Application No. PCT/CN/2010/001083, dated Oct. 10, 2010, 12 pages total.

* cited by examiner

ARTIFICIAL CERVICAL VERTEBRAE COMPOSITE JOINT

CROSS-REFERENCE TO RELATED APPLICATION

This Application is a Section 371 National Stage Application of International Application No. PCT/CN2010/001083, filed Jul. 19, 2010 and published as WO 2011/015031 Al Feb. 2, 2011, in Chinese, the contents of which are hereby incorporated by reference in their entirety.

BACKGROUND OF THE INVENTION

1. Field of the Invention

The present invention relates to a device for reconstructing cervical vertebrae after subtotal resection of cervical vertebrae body, and particularly to an artificial cervical vertebrae composite joint. The artificial cervical vertebrae composite joint is achieved by means of bionics of physiological reconstruction in three aspects of anatomy, stability and motion of cervical vertebrae by simulating normal cervical vertebrae.

2. Description of the Related Art

Clinically, subtotal resection of cervical vertebrae body mostly needs to be performed for infection, tumor, and degenerative disease of cervical vertebrae and then the resected segment of the cervical vertebrae needs to be reconstructed. Currently, reconstruction methods clinically commonly used mainly comprise two methods, that is, segmental bone graft fusion and replacement of artificial vertebral body. A method of bone graft fusion as a current standard method of clinically reconstructing cervical vertebrae after subtotal resection of cervical vertebrae body is to fill a defect segment with autograft bone issue or xenoma bone issue while adding internal fixation to reconstruct stability of the cervical vertebrae. The method achieves reconstruction of stability of the cervical vertebrae by bone fusion between the grafted bone and upper and lower cervical vertebrae bodies to eliminate pain. However, the reconstruction method is not ideal anatomical reconstruction and causes the reconstructed segment to lose movability completely and thus affects entire movement function of the cervical vertebrae. In addition, the method also results in degradation of intervertebral disk of adjacent segments due to stress concentration in the long term. There are various designs of artificial vertebral body so far, but in all of the designs, stability of cervical vertebrae is reconstructed by means of bone graft fusion, self fixation or additional internal fixation and there are the problems that movability of the segment is lost and intervertebral disk of adjacent segments degrades in the long term. Therefore, the reconstruction of the various designs is not real physiological reconstruction. All of few artificial vertebral bodies designed in consideration of motion reconstruction finally fail due to their motion mode different from physiological motion mode or bad stability. Currently, clinical non-fusion reconstruction has become development trend. Based on the reconstruction, products such as artificial hip, knee, ankle, and elbow joints and artificial intervertebral disk are produced, and are clinically largely applied to achieve quick cure, good effect, and stable clinical long-term effect. Generation of the artificial intervertebral disk undoubtedly has epochal significance for vertebral column surgery. Currently, the artificial intervertebral disk has gadually matured. Non-fusion reconstruction of a single segment of cervical vertebrae generates excellent products such as Bryandisc and Prestige. However, currently, there has not yet been a good method to solve the problem of non-fusion reconstructing after subtotal resection of cervical vertebrae. Therefore, the present applicant designed an artificial cervical vertebrae composite joint in prophase. It is manifested by primary biomechanical to research that a ball-and-socket joint of the artificial cervical vertebrae composite joint retains movability of the cervical vertebrae to a certain degree and that a new concept is provided in the way of the non-fusion reconstruction. Based on the design, the present applicant further researches normal motion mode of cervical vertebrae and concludes by synthesizing past research that motion of the cervical vertebrae is not simple rotation, but is a coupling motion of rotation and translation. The rotation is coupled with relative displacement between adjacent cervical vertebrae bodies while the adjacent cervical vertebrae bodies rotate, and the upper cervical vertebrae body has a variable center of rotation relative to the lower cervical vertebrae body. Therefore, the primary design of the artificial cervical vertebrae composite joint, that is, the ball-and-socket joint, has a fixed center of rotation, and the motion mode of the joint is a simple rotation, and greatly different from the motion mode of normal cervical vertebra.

According to document retrieval made by the present applicant, so far there is not a method capable of designing the joint in consideration of stability, movability, and particular coupling motion mode of cervical vertebrae to really achieve physiological reconstruction. Only if a particular artificial joint is designed to simulate the motion mode of the normal cervical vertebra, bionics of the reconstruction of the cervical vertebrae is really achieved.

SUMMARY OF THE INVENTION

An object of the present invention is to provide an artificial cervical vertebrae composite joint capable of restoring movability between cervical vertebrae bodies and achieving physiological reconstruction of the cervical vertebrae bodies by "remanufacturing" original intervertebral disk and cervical vertebrae body, thereby not only restoring anatomical sequence and stability of the cervical vertebrae, but also retaining normal physiological movability of a defect segment.

In order to achieve the above object, the present invention employs the following technical solution.

An artificial cervical vertebrae composite joint is characterized in that the artificial cervical vertebrae composite joint is composed of two upper and lower fixing members disposed vertically symmetrically, a cervical vertebrae body member, and two connection members, the cervical vertebrae body member being connected between the fixing members through the connection members;

the fixing members each have an L shape and comprise a front wing part and a base part, a locking screw hole is formed in the front wing part of each of the fixing members, and a protruded inverted tooth-shaped skidproof groove is disposed on a middle portion of the base part of each of the fixing members;

a bone grafting hole is transversely disposed through a middle portion of the cervical vertebrae body member, cavities are disposed on both upper and lower sides of the cervical vertebrae body member at an axial center of the cervical vertebrae body member to mount the connection members, and each cavity comprises a cylindrical recessed chamber and a spherical protrusion located at a center of a bottom surface of the recessed chamber;

the connection member is shaped to comprise a cylindrical body and a spherical structure, the spherical structure comprises a concave spherical surface coinciding with the spherical protrusion located within the cavity of the cervical vertebrae body member; positioning pin locking holes are disposed on both sides of the cervical vertebrae body member, respectively, a fixing ring locking hole is disposed in a fixing ring, and the fixing ring is locked in the recessed chamber by means of a positioning pin; and the connection member has one end mounted in the cavity by means of the fixing ring, and another end connected with the fixing member to form a stable sliding-trough type ball-and-socket joint.

A mode of relative motion between the fixing member and the cervical vertebrae body member is slide of the spherical structure of the connection member along the spherical protrusion located within the cavity of the cervical vertebrae body member.

The spherical structure of the connection member rotates along the spherical protrusion located within the cavity of the cervical vertebrae body member, an angle range of rotary motion of 0-14 degrees is generated between the fixing member and the cervical vertebrae body member in every direction, the cylindrical body of the connection member swings in a range of a clearance between the cylindrical body and the fixing ring, and a displacement in a range of 0-2 mm is generated between the fixing member and the cervical vertebrae body member, thereby forming a coupling motion mode of the sliding-trough type ball-and-socket joint.

The artificial cervical vertebrae composite joint according to the present invention brings about the technical characteristic that the normal coupling motion mode of the segment of the cervical vertebrae is restored while reconstructing stability of the cervical vertebrae to reach real physiological reconstruction. It is hopeful that the present invention will substitute for the existing method of bone graft fusion and become a standard method of clinically reconstructing vertebral body.

Figure 1:
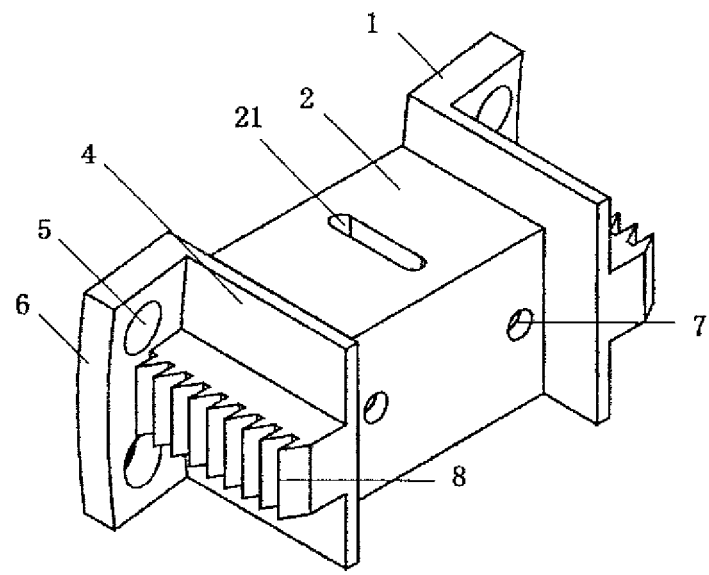
FIG. 1 is a schematic view of external structure of an artificial cervical vertebrae composite joint according to the present invention.
Figure 2:
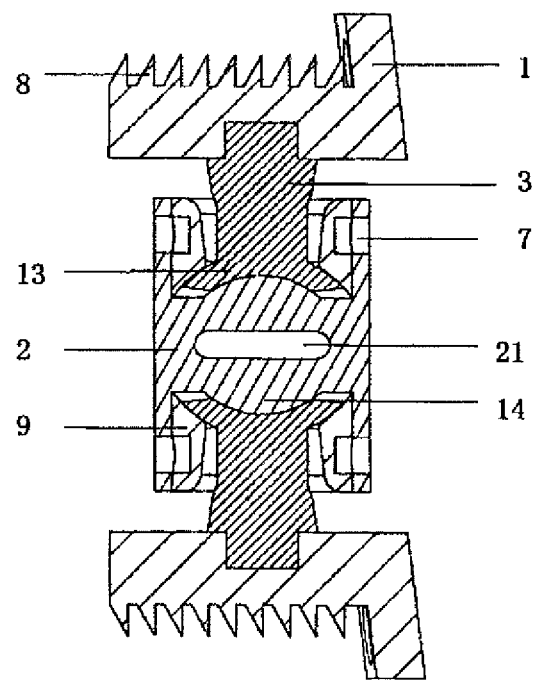
FIG. 2 is a sectional view of FIG. 1 taken vertically.
Figure 3:
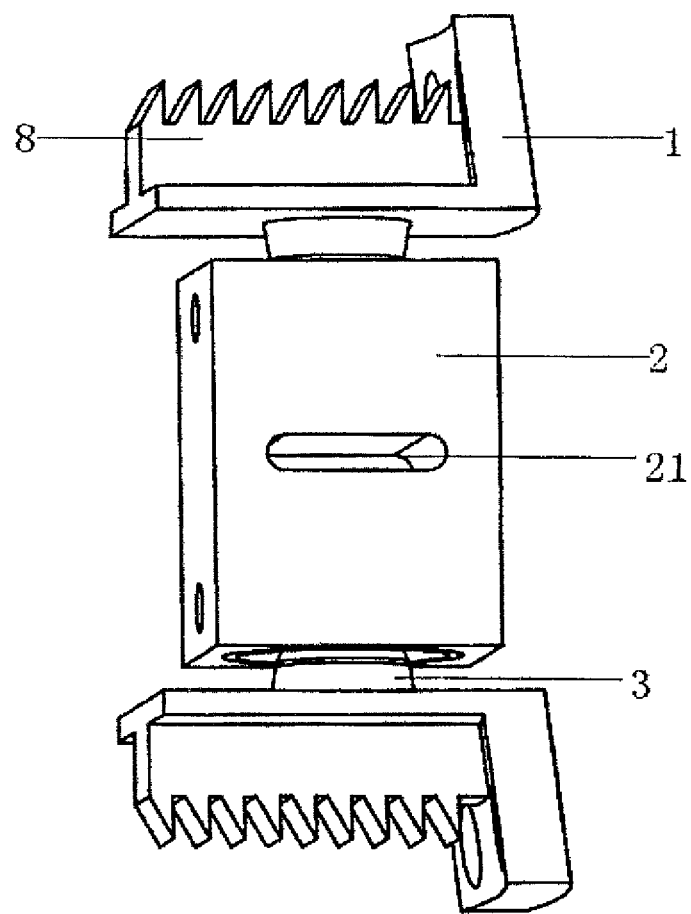
FIG. 3 is a schematic view of lateral structure of the artificial cervical vertebrae composite joint shown in FIG. 1.
Figure 4:
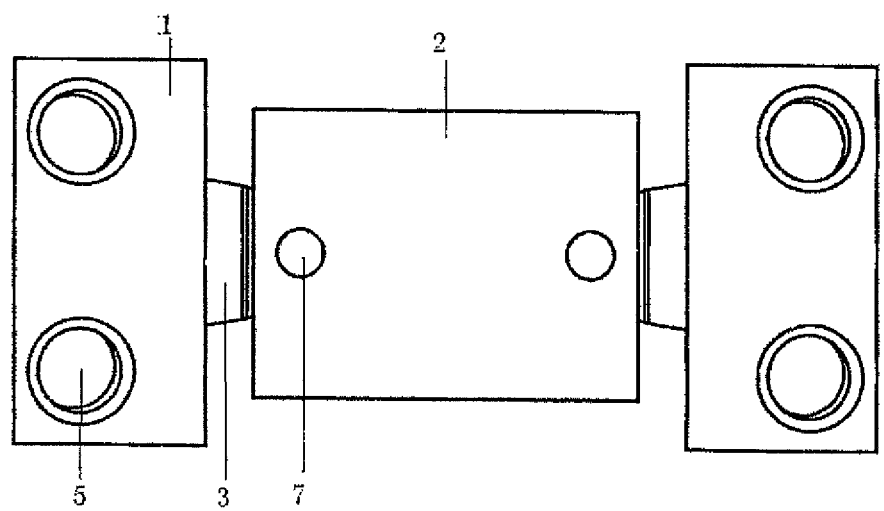
FIG. 4 is a schematic view of front structure of the artificial cervical vertebrae composite joint shown in FIG. 1.

In the drawings, the following reference numerals indicate the respective elements: 1. a fixing member; 2, a cervical vertebrae body member; 3. a connection member; 4. a base part of the fixing member; 5. a locking screw hole; 6. a front wing part of the fixing member; 7. a positioning pin locking hole; 8. an inverted tooth-shaped skidproof groove; 9. a fixing ring; 10. a fixing ring locking hole; 11. an arc-shaped surface of the fixing ring; 12. a cylindrical body of the connection member; 13. a spherical structure; 14. a spherical protrusion; 15. a concave spherical surface; 16. a cylindrical recessed chamber; 17. an outlet diameter of the fixing ring; 18. an inlet diameter of the fixing ring; 19; a diameter of the cylindrical body; 20. a chord corresponding to an arc of a section of the spherical structure; and 21. a bone grafting hole.

A further description of the present invention will be made as below with reference to embodiments of the invention taken in conjunction with the accompanying drawings.

DETAILED DESCRIPTION OF THE EMBODIMENTS

It is manifested by research that it cannot radically solve the difficult problem of physiological reconstruction of cervical vertebrae to reconstruct a defect segment corresponding to two intervertebral disks and a single cervical vertebrae body by simple replacement of the cervical vertebrae body and bone graft fusion. Only if original intervertebral disk and cervical vertebrae body are completely "remanufactured" to restore movability of an intervertebral joint, the cervical vertebrae can be really physiologically reconstructed.

As illustrated in FIG. 1, an artificial cervical vertebrae composite joint according to the present invention is composed of two upper and lower fixing members 1 disposed vertically symmetrically, a cervical vertebrae body member 2, and two connection members 3, the cervical vertebrae body member 2 is connected between the fixing members 1 through the connection members 3.

The fixing members 1 each have an L shape and comprise a front wing part 6 and a base part 4, a locking screw hole 5 is formed in the front wing part 6 of each of the fixing members, and a protruded inverted tooth-shaped skidproof groove 8 is disposed on a middle portion of the base part 4 of each of the fixing members.

The cervical vertebrae body member has a vertically symmetrical structure, a bone grafting hole 21 is transversely disposed through a middle portion of the cervical vertebrae body member 2, cavities are disposed on both upper and lower sides of the cervical vertebrae body member 2 at an axial center of the cervical vertebrae body member 2 to mount the connection members 3, and each cavity comprises a cylindrical recessed chamber 16 and a spherical protrusion 14 located at a center of a bottom surface of the recessed chamber.

The connection member 3 is shaped to comprise a cylindrical body 12 and a spherical structure 13, and the spherical structure 13 comprises a concave spherical surface 15 coinciding with the spherical protrusion 14 located within the cavity of the cervical vertebrae body member.

Positioning pin locking holes 7 are disposed on both sides of the cervical vertebrae body member 2, respectively, a fixing ring locking hole 10 is disposed in a fixing ring 9, and the fixing ring 9 is locked in the recessed chamber by means of a positioning pin; and the connection member 3 has an end mounted in the cavity by means of the fixing ring 9, and another end connected with the fixing member 1 to form a stable sliding-trough type ball-and-socket joint.

The concave spherical surface 15 and the spherical protrusion 14 located within the cavity of the cervical vertebrae body member are concentric. A difference between a radius of the spherical structure 13 and a radius of the spherical protrusion 14 is 1 mm, that is, a thickness of the spherical structure 13. A diameter 17 of an outlet of the fixing ring is 2 mm larger than a diameter 19 of the cylindrical body of the connection member. However, a diameter 18 of an inlet of the fixing ring is less than a length of a chord 20 corresponding to an arc of a section of the spherical structure 13, thereby not only ensuring that the cylindrical body 12 of the connection member will not escape when the joint slides, but also achieving relative displacement between the fixing member 1 and the cervical vertebrae body member 2 while the joint rotates. The displacement is performed in such a way that the spherical structure 13 of the connection member slides along the spherical protrusion 14 of the cervical vertebrae body member.

The spherical structure 13 of the connection member 3 rotates along the spherical protrusion 14 located within the cavity of the cervical vertebrae body member, an angle range of rotary motion of 0-14 degrees is generated between the fixing member 1 and the cervical vertebrae body member 2 in every direction, the cylindrical body 12 of the connection member swings in a range of a clearance between the cylindrical body 12 and the fixing ring 9, and a displacement in a range of 0-2 mm is generated between the fixing member 1 and the cervical vertebrae body member 2, thereby forming a coupling motion mode of the sliding-trough type ball-and-socket joint.

The following embodiment is a specific embodiment provided by the inventor. It is noted that the present invention is not limited to the specific embodiment.

FIGS. 1, 2, 3, and 4 show configuration of an artificial cervical vertebrae composite joint according to the embodiment. The artificial cervical vertebrae composite joint is composed of two symmetrical fixing members 1, a middle cervical vertebrae body member 2, and two connection members 3. The fixing members 1 each have an L shape and comprise a front wing part 6 and a base part 4. Two locking screw holes 5 are formed in the front wing part 6 of each of the fixing members. An angle between the front wing part 6 and the base part 4 of the upper fixing member and an angle between the front wing part 6 and the base part 4 of the lower fixing member are different from each other, and 80 degrees and 100 degrees respectively to accommodate normal curvature of cervical vertebrae. An inverted tooth-shaped skidproof groove 8 is disposed at a center of the base part 4 of each of the fixing members to fix an artificial cervical vertebrae composite joint system. A cylindrical body 12 is connected with a center of the base part 4 of each of the fixing is members on a side opposite to the front wing part 6 of the corresponding fixing member. The connection member 3 has the cylindrical body 12, and a spherical structure 13 including a concave spherical surface 15. The cervical vertebrae body member 2 is configured in a rectangular parallelepiped, cavities are disposed at an axial center of the cervical vertebrae body member 2 on both upper and lower sides of the cervical vertebrae body member 2 to mount the connection members 3, do not communicate with each other, and each cavity comprises a cylindrical recessed chamber 16 and a spherical protrusion 14 located at a center of a bottom surface of the recessed chamber. The spherical structure 13 of the connection member 3 and the spherical protrusion 14 are closely combined between the connection member 1 and the cervical vertebrae body member 2. Positioning pin locking holes 7 are disposed on both sides of the cervical vertebrae body member 2, respectively. A fixing ring locking hole 10 is disposed in a fixing ring 9. The fixing ring 9 is locked in the recessed chamber by means of a positioning pin. The connection member 3 has an end mounted in the cavity by means of the fixing ring 9, and another end connected with the fixing member 1 to form a stable sliding-trough type ball-and-socket joint.

During fabrication, the concave spherical surface 15 of the connection member 3 and the spherical protrusion 14 located at a center of a bottom surface of the cylindrical recessed chamber 16 of the cervical vertebrae body member 2 should be set to be concentric, a diameter 17 of an outlet of the fixing ring is 2 mm larger than a diameter 19 of the cylindrical body of the connection member. However, a diameter 18 of an inlet of the fixing ring is less than a length of a chord 20 corresponding to an arc of a section of the spherical structure 13, thereby not only ensuring that the cylindrical body 12 of the connection member will not escape when the joint slides, but also achieving relative displacement between the fixing member 1 and the cervical vertebrae body member 2 while the joint rotates. The displacement is performed in such a way that the spherical structure 13 of the connection member slides along the spherical protrusion 14 of the cervical vertebrae body member. In addition, there should be an angle range of rotary motion of 0-14 degrees between the fixing member 1 and the cervical vertebrae body member 2 in every direction, and a displacement in a range of 0-2 mm is generated between the fixing member 1 and the cervical vertebrae body member 2 while rotating, thereby forming a coupling motion mode of the sliding-groove type ball-and-socket joint. The maximal displacement is a difference between the diameter 17 of the outlet of the fixing ring and the diameter 19 of the cylindrical body of the connection member 3. A bone grafting hole 21 is transversely disposed through a middle portion of the cervical vertebrae body member 2 to graft bone.

Figure 5:
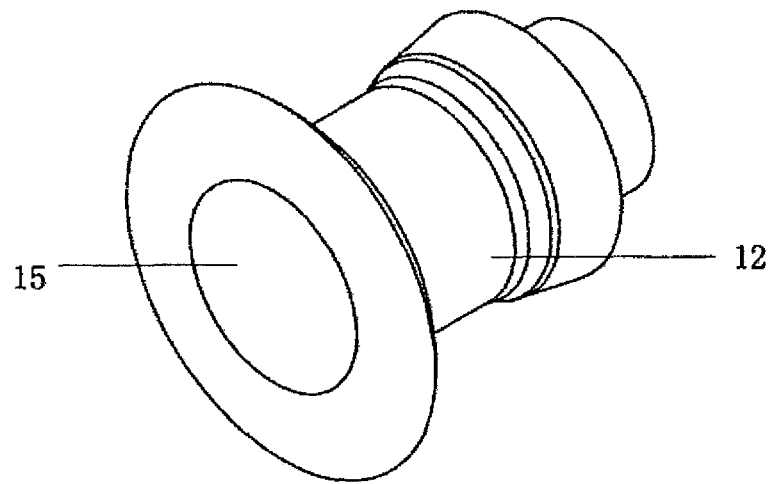
FIG. 5 is a schematic perspective view of structure of a spherical surface of a fixing member shown in FIG. 1.
Figure 6:
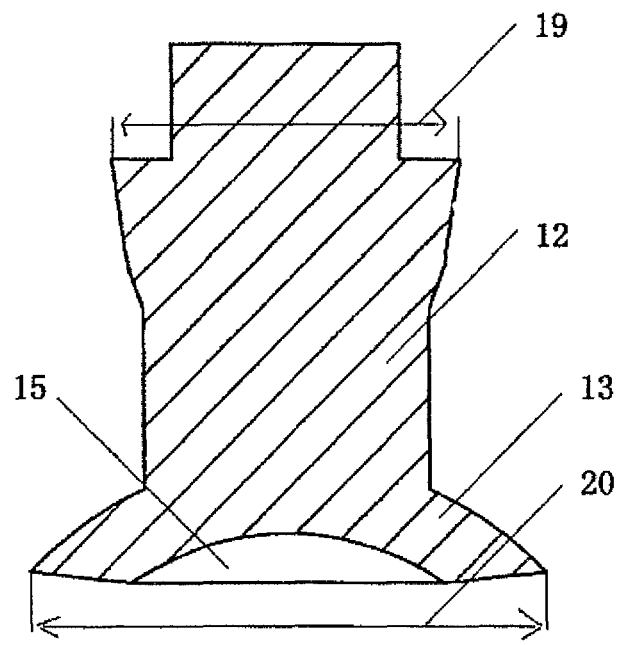
FIG. 6 is a vertically-taken sectional view of the spherical surface of the fixing member shown in FIG. 1.

As illustrated in FIGS. 5 and 6, the connection member 3 is shaped to comprise the cylindrical body 12 and the spherical structure 13, and the spherical structure 13 comprises the concave spherical surface 15 coinciding with the spherical protrusion 14 located within the cavity of the cervical vertebrae body member. The center of the base part 4 of each of the fixing members on the side opposite to the front wing part 6 of the corresponding fixing member is connected with the cylindrical body 12 of the connection member by means of screw thread. The concave spherical surface 15 of the connection member 3 and the spherical protrusion 14 located at the center of the bottom surface of the cylindrical recessed chamber 16 of the cervical vertebrae body member 2 are concentric. A difference between a radius of the spherical structure 13 and a radius of the spherical protrusion 14 is limn, that is, a thickness of the spherical structure 13.

Figure 7:
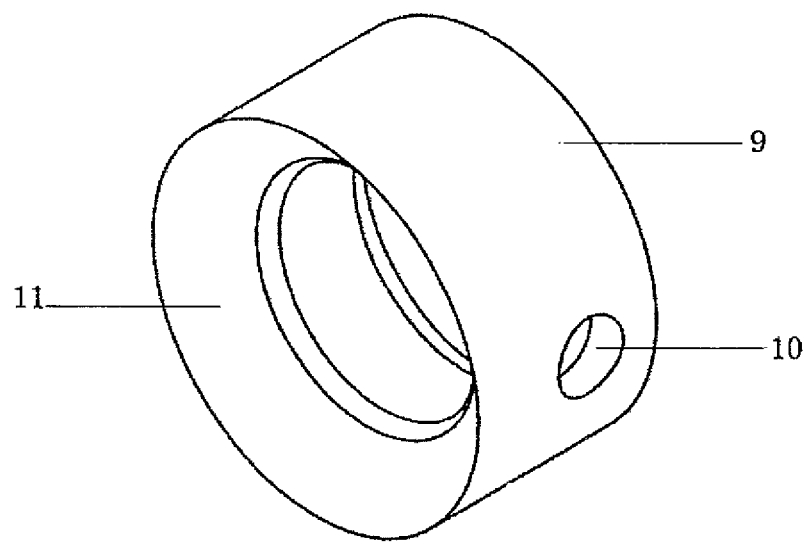
FIG. 7 is a schematic isometric axonometric view of structure of a fixing ring shown in FIG. 1.

As illustrated in FIG. 7, the fixing ring is configured in a circular ring. The diameter 17 of the outlet of the fixing ring is 2 mm larger than the diameter 19 of the cylindrical body of the connection member, but the diameter 18 of the inlet of the fixing ring is less than the length of the chord 20 corresponding to the arc of the section of the spherical structure 13. An arc-shaped surface 11 of a lower surface of the fixing ring is in contact with the spherical structure 13, and the fixing ring 9 is locked by a positioning pin through a fixing ring locking hole 10 to form a stable sliding-trough type ball-and-socket joint.

Figure 8:
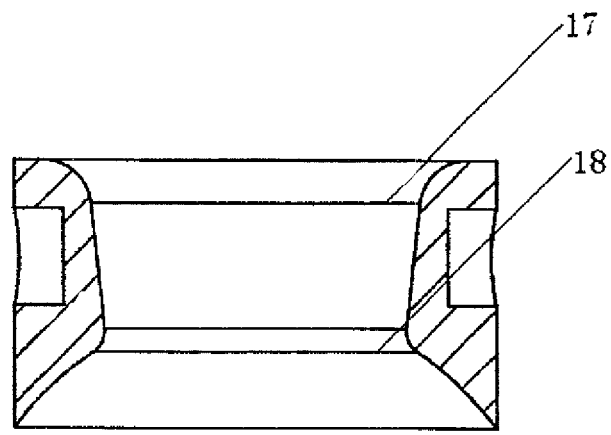
FIG. 8 is a vertically-taken sectional view of the fixing ring shown in FIG. 1.

As illustrated in FIG. 8, the fixing member 1 is configured such that the fixing member 1 has an L shape. The front wing part 6 of the fixing member has an arc to be capable of coinciding with a front edge of the cervical vertebrae body better. The two locking screw holes 5 are formed in the front wing part 6 of the fixing member. Locking screws are implanted into the cervical vertebrae body through the locking screw holes 5. The angle between the front wing part 6 and the base part 4 of the upper fixing member and the angle between the front wing part 6 and the base part 4 of the lower fixing member are different from each other, and 80 degrees and 100 degrees respectively to accommodate change in normal curvature of cervical vertebrae. The inverted tooth-shaped skidproof groove 8 is disposed at the center of the base part 4 of each of the fixing members on the same side as the front wing part to fix the artificial cervical vertebrae composite joint.

Figure 9:
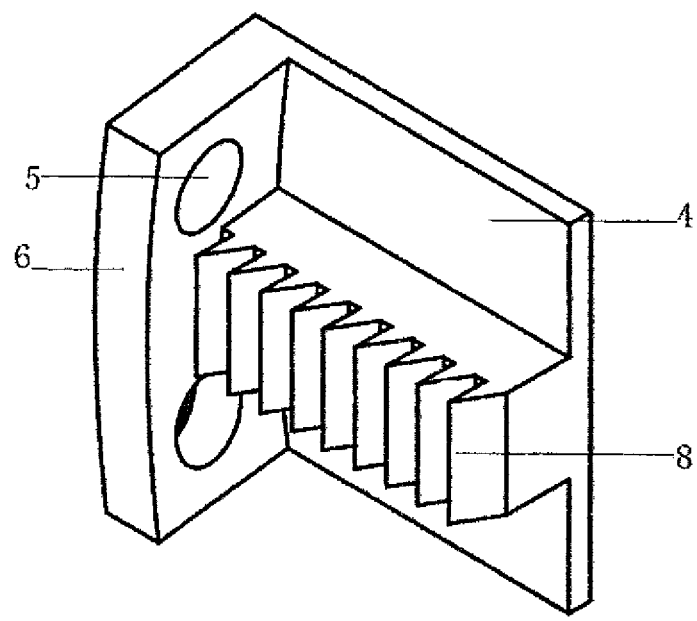
FIG. 9 is a schematic isometric axonometric view of structure of a fixing member shown in FIG. 1.
Figure 10:
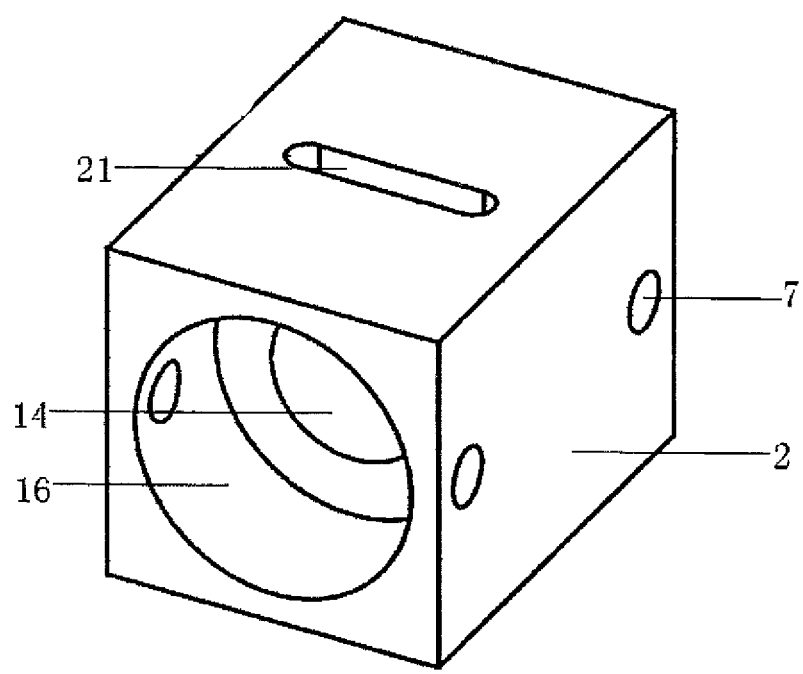
FIG. 10 is a schematic isometric axonometric view of structure of a cervical vertebrae body member shown in FIG. 1.

As illustrated in FIG. 9, the cervical vertebrae body member 2 is configured in a rectangular parallelepiped, the bone grafting hole 21 is transversely disposed through the middle portion of the cervical vertebrae body member 2, and the cavities are disposed on both the upper and lower sides of the cervical vertebrae body member 2 at the axial center of the cervical vertebrae body member 2 to mount the connection members 3, and each cavity comprises the cylindrical recessed chamber 16 and the spherical protrusion 14 located at the center of the bottom surface of the recessed chamber. The positioning pin passes through the positioning pin locking hole 7 and terminates at the fixing ring locking hole 10 to lock the fixing ring 9. A rough coating of hydroxyapatite is formed around the bone grafting hole 21 of the cervical vertebrae body member 2.

The artificial cervical vertebrae composite joint fabricated according to the embodiment achieves physiological reconstruction of cervical vertebrae. Firstly, the structure achieves stability and restores physiological movability of the cervical vertebrae. Secondly, the structure generates relative displacement between the cylindrical body 12 of the connection member and the spherical protrusion 14 located on the bottom surface of the cavity of the cervical vertebrae body member 2 while sliding. An amount of the displacement is limited by the fixing ring 9 to ensure the stability of the joint and physiological reconstruction of a motion mode of the cervical vertebrae.

The artificial cervical vertebrae composite joint fabricated according to the embodiment is made of material selected from cobalt-chrome-molybdenum alloy.

The artificial cervical vertebrae composite joint of the present invention works on the following principle. During implantation, screws are implanted into adjacent normal vertebral body through intervertebral disk via the locking screw holes 5 of the front wing parts 6 of the fixing members, and locked by screw thread of the locking screw holes, and the inverted tooth-shaped skidproof groove 8 is closely combined with the adjacent normal vertebral body to obtain immediate stability of the fixing members 1. A long-term stability is obtained by inducing growing of bone by means of porous coating of titanium located on back sides of the base parts 4 of the fixing members. Immediate stability of the cervical vertebrae body member 2 is achieved by strong friction of a rough coating of hydroxyapatite located on a side of the cervical vertebrae body member. Long-term stability of the vertebral body is achieved by fusion between grafted bone in a through bone grafting conduit and the partial vertebral body remaining on both ends of the vertebral body after subtotal resection, and by growing of bone on a lateral rough surface. A stable sliding-trough type ball-and-socket joint is formed by locking by means of the fixing ring 9 and the positioning pin, so that it is difficult for the sliding-trough type ball-and-socket joint to be dislocated, thereby reaching short-term and long-term stability of intervertebral joints. Therefore, anatomical reconstruction of the intervertebral disk and the cylindrical body restores both stability of the cervical vertebrae and movability of the intervertebral joints and achieves relative displacement between vertebral bodies during motion. The coupling motion mode of the joint reaches an effect of simulating a motion mode of normal cervical vertebrae.

What is claimed is:

1. An artificial cervical vertebrae composite joint, comprising:
    upper and lower fixing members disposed symmetrically to each other,
    a cervical vertebrae body member having upper and lower sides, and
    upper and lower connection members, the cervical vertebrae body member being connected between the fixing members through the connection members,
    wherein the fixing members each have an L shape and comprise a front wing part and a base part, an angle between the front wing part and the base part of the upper fixing member and an angle between the front wing part and the base part of the lower fixing member are different from each other, a locking screw hole is formed in the front wing part of each of the fixing members, and teeth are disposed on a middle portion of the base part of each of the fixing members;
    wherein a bone grafting hole is transversely disposed relative to an axial direction of the cervical vertebrae body member through a middle portion of the cervical vertebrae body member, the cervical vertebrae body member has an upper cavity disposed on the upper side of the cervical vertebrae body member at an axial center of the cervical vertebrae body member to mount the upper connection member, and a lower cavity disposed on the lower side of the cervical vertebrae body member at the axial center of the cervical vertebrae body member to mount the lower connection member, and the upper cavity comprises a first cylindrical recessed chamber and a first spherical protrusion, wherein the first spherical protrusion is located at a center of a bottom surface of the first recessed chamber, and the lower cavity comprises a second cylindrical recessed chamber and a second spherical protrusion, wherein the second spherical protrusion is located at a center of a bottom surface of the second recessed chamber;
    wherein the upper connection member comprises a first cylindrical body and a first spherical structure, the first spherical structure comprises a first concave spherical surface coinciding, with the first spherical protrusion located within the upper cavity of the cervical vertebrae body member;
    wherein the lower connection member comprises a second cylindrical body and a second spherical structure, the second spherical structure comprises a second concave spherical surface coinciding with the second spherical protrusion located within the lower cavity of the cervical vertebrae body member;
    wherein the artificial cervical vertebrae composite joint further comprising:
        a first positioning pin locking hole disposed on the upper side of the cervical vertebrae body member;
        a second positioning pin locking hole disposed on the lower side of the cervical vertebrae body member;
        a first fixing ring in which a first fixing ring locking hole is disposed, wherein the first fixing, ring is locked in the first recessed chamber of the cervical vertebrae body member by a first positioning pin; and
        a second fixing ring in which a second fixing ring locking hole is disposed, wherein the second fixing ring is locked in the second recessed chamber of the cervical vertebrae body member by a second positioning pin;
    wherein the upper connection member has an end mounted in the upper cavity by means of the first fixing ring, and another end connected with the upper fixing member to form a stable sliding-trough type ball-and-socket joint;
    wherein the lower connection member has an end mounted in the lower cavity by means of the second fixing ring, and another end connected with the lower fixing member to form a stable sliding-trough type ball-and-socket joint;

wherein the first fixing ring is disposed on a side of the first spherical structure of the upper connection member opposite to the first spherical protrusion, the first cylindrical body of the upper connection member is disposed in a hole of the first fixing ring, and the first spherical structure of the upper connection member has a diameter larger than that of the hole of the first fixing ring; and wherein the second fixing ring is disposed on a side of the second spherical structure of the lower connection member opposite to the second spherical protrusion, the second cylindrical body of the lower connection member is disposed in a hole of the second fixing ring, and the second spherical structure of the lower connection member has a diameter larger than that of the hole of the second fixing ring.

2. The artificial cervical vertebrae composite joint of claim 1, wherein each of the upper and lower fixing members and the cervical vertebrae body member have an angle range of relative rotary motion between 0-14 degrees, and a relative displacement in a range of 0-2 mm.

3. The artificial cervical vertebrae composite joint of claim 1, wherein the first concave spherical surface and the first spherical protrusion are concentric, and the second concave spherical surface and the second spherical protrusion are concentric.

4. The artificial cervical vertebrae composite joint of claim 1, wherein the first fixing ring has a diameter, which is 2 mm larger than a diameter of the first cylindrical body of the upper connection member, on a side close to the upper fixing member, and a diameter, which is less than a diameter of the first spherical structure of the upper connection member, on a side close to the first spherical protrusion of the cervical body member, and wherein the second fixing ring has a diameter which is 2 mm larger than a diameter of the second cylindrical body of the lower connection member, on a side close to the lower fixing member, and a diameter, which is less than a diameter of the second spherical structure of the lower connection member, on a side close to the second spherical protrusion of the cervical body member.

5. The artificial cervical vertebrae composite joint of claim 1, wherein the cervical vertebrae body member is a rectangular parallelepiped, and has a side with a rough coating of hydroxyapatite.

6. The artificial cervical vertebrae composite joint of claim 1, wherein the teeth of each of the fixing members are inclined towards the front wing part.

7. The artificial cervical vertebrae composite joint of claim 1, wherein the angle between the front wing part and the base part of the upper fixing member is about 80 degrees, and the angle between the front wing part and the base part of the lower fixing member is about 100 degrees.

\* \* \* \* \*